United States Patent [19]
Chapura et al.

[11] Patent Number: 5,128,140
[45] Date of Patent: Jul. 7, 1992

[54] SWALLOWABLE PHARMACEUTICAL COMPOSITIONS

[75] Inventors: Francis B. Chapura, Hamilton; Sekhar Mitra, Cincinnati, both of Ohio

[73] Assignee: The Procter & Gamble Company, Cincinnati, Ohio

[21] Appl. No.: 641,030

[22] Filed: Jan. 14, 1991

[51] Int. Cl.$^5$ ............................................. A61R 9/48
[52] U.S. Cl. ........................... 424/451; 424/456; 424/489; 424/653
[58] Field of Search ............... 424/653, 489, 456, 451

[56] References Cited
U.S. PATENT DOCUMENTS

| | | | |
|---|---|---|---|
| 4,496,571 | 1/1985 | Yellin et al. | 514/258 |
| 4,801,454 | 1/1989 | Coveney | 424/653 |
| 4,801,608 | 1/1989 | Bos et al. | 424/653 |

*Primary Examiner*—Thurman K. Page
*Assistant Examiner*—Leon R. Horne
*Attorney, Agent, or Firm*—Kim William Zerby; Douglas C. Mohl; Richard C. Witte

[57] ABSTRACT

Oral pharmaceutical compositions in unit dosage form suitable for swallowing (especially capsules) comprising a safe and effective amount of a soluble bismuth-containing pharmaceutical agent (preferably a pharmaceutically-acceptable salt suitable for oral co-administration of bismuth and an H$_2$ receptor blocking anti-secretory agent), and optionally one or more pharmaceutically-acceptable carrier materials, wherein the packing density of the dosage unit is less than about 1 g/ml.

27 Claims, No Drawings

SWALLOWABLE PHARMACEUTICAL COMPOSITIONS

BACKGROUND OF THE INVENTION

The present invention relates to low density (less than about 1 g/ml) oral pharmaceutical compositions in unit dosage form suitable for swallowing comprising a soluble bismuth-containing pharmaceutical agent, preferably a soluble bismuth-containing pharmaceutically-acceptable salt suitable for oral co-administration of bismuth and an $H_2$ receptor blocking anti-secretory agent, with said salts comprising bismuth, an organic acid, and an $H_2$ receptor blocking anti-secretory agent (preferably selected from the group consisting of ranitidine or cimetidine).

Soluble bismuth-containing pharmaceutical agents are known. Colloidal bismuth subcitrate is described, for example, in European Patent 0,075,992, U.S. Pat. No. 4,801,608, and Great Britain Patent 1,478,742. Pharmaceutically-acceptable salts suitable for oral co-administration of bismuth and an $H_2$ receptor blocking anti-secretory agent are described in European Patent Application Publication No. 282,132. Furthermore, such salts comprising ranitidine are also described in Great Britain Patent Application Publication No. 2,220,937.

It has been reported that the highly water soluble bismuth-containing agent colloidal bismuth subcitrate ("CBS"), when dosed as a swallowable tablet, produces a transient sharp peak of bismuth blood level in humans after ingestion (see C. U. Nwokolo et al., *Aliment. Pharmacol. Therap.*, 3, 1989, 29–39). It has been discovered that this tablet form of CBS (which has a density greater than 1 g/ml), in vitro in a liquid acidic medium, has a tendency to sink to the bottom of the liquid and dissolve by first forming liquid CBS solution rather than the desired insoluble bismuth precipitate. It has also been discovered that, by contrast, unit dosage forms which are less dense than this tablet form and also less dense than the acidic medium (about 1 g/ml) do not form this initial CBS liquid but rather quickly forms the desired insoluble bismuth precipitate. Interestingly, when these low density unit dosage forms are weighted to the bottom of the test liquid, again the CBS initially liquifies. In vivo testing confirms that in fact these low density unit dosage forms substantially reduce bismuth blood levels as predicted by these different in vitro characteristics. On the other hand, bismuth subsalicylate which is essentially insoluble in water does not behave similarly.

Therefore, the oral dosage units of the present invention comprising soluble bismuth-containing phrmaceutical agents and having low packing density surprisingly give peak bismuth plasma levels and a total bismuth absorption which are lower than that of denser dosage units. This is contrary to what one might expect—that less dense and thereby more dispersible material would lead to more rapid dissolution and consequently to greater absorption than compressing to higher density the same material. It is also contrary to the current tendency in the art of pharmaceutical production, which is to concentrate the oral dosage units, e.g. by compressing the contents of oral capsules to a high density (see Hard Capsules, Development and Technology, Ed. K. Ridgway 1987, chapter 9, G. C. Cole, pp. 92–103).

An object of the present invention therefore is to provide an oral dosage unit suitable for swallowing which minimizes bismuth absorption comprising a soluble bismuth-containing pharmaceutical agent. Preferred soluble bismuth-containing pharmaceutical agents are colloidal bismuth subcitrate and pharmaceutically-acceptable salts suitable for oral co-administration of bismuth and an $H_2$-receptor blocking anti-secretory agent.

This and other objects of the present invention will become readily apparent from the detailed description which follows.

All percentages and ratios used herein are by weight, and all measurements made at 25° C., unless otherwise specified.

SUMMARY OF THE INVENTION

The present invention relates to oral pharmaceutical compositions in unit dosage form suitable for swallowing comprising a safe and effective amount of a soluble bismuth-containing pharmaceutical agent (preferably a pharmaceutically-acceptable salt suitable for oral co-administration of bismuth and an $H_2$ receptor blocking anti-secretory agent) and, optionally, pharmaceutically-acceptable carrier materials, wherein the packing density of the pharmaceutical composition is less than about 1 g/ml.

The present invention also relates to a method for manufacturing unit dosage forms suitable for swallowing comprising a soluble bismuth-containing pharmaceutical agent. Said method comprises the step of forming a unit dosage of a dry composition comprising a soluble bismuth-containing pharmaceutical agent having a packing density of less than about 1 g/ml. Preferred is the method wherein a dry particulate composition comprising a soluble bismuth-containing pharmaceutical agent is filled into a capsule to a packing density of less than about 1 g/ml.

The present invention further relates to methods for treating or preventing gastrointestinal disorders in humans or lower animals. These methods comprise orally administering by swallowing to a human or lower animal in need of such treatment or prevention a safe and effective amount of an oral pharmaceutical composition according to the present invention.

DETAILED DESCRIPTION OF THE INVENTION

(1) Oral Pharmaceutical Compositions

The oral pharmaceutical compositions of the present invention comprise a soluble bismuth-containing pharmaceutical agent (preferably a pharmaceutically-acceptable salt suitable for oral co-administration of bismuth and an $H_2$ receptor blocking anti-secretory agent) in unit dosage forms suitable for swallowing (e.g., tablets and, especially, capsules) wherein the packing density of the composition is less than about 1 g/ml. Preferably, these compositions comprise the pharmaceutically-acceptable salt and a pharmaceutically-acceptable carrier material(s).

The term "packing density," as used herein, means the weight of the drug mixture (soluble bismuth-containing pharmaceutical agent ingredient plus carrier materials) in grams divided by the volume occupied by the dose form expressed in milliliters, and, in case of a filled capsule form, excludes the volume and weight of the capsule container. Thus, the packing density can be varied by varying the types and amounts of excipients added to the soluble bismuth-containing pharmaceutical agent and especially by varying the pressure used in compressing the units. Oral pharmaceutical compositions herein have packing density of less than about 1 g/ml, preferably within the range of from about 0.05 g/ml to less than about 1 g/ml, and more preferably from about 0.5 g/ml to about 0.75 g/ml.

The particular agents for use herein, as well as the levels and amounts preferred therefor, are described in greater detail hereinafter.

(a) Soluble Bismuth-Containing Pharmaceutical Agent

Pharmaceutical compositions of the present invention comprise a soluble bismuth-containing pharmaceutical agent. The term "soluble bismuth-containing pharmaceutical agent", as used herein, means any pharmaceutical agent safe and effective for oral administration to a human or lower animal comprising bismuth such that the bismuth is soluble in water at a level of at least about 0.5% (weight of bismuth/volume water) within the pH range of from about 4 to about 8, and wherein said agent's pharmaceutical efficacy does not require systemic bismuth absorption. Preferred soluble bismuth-containing pharmaceutical agents are soluble in water at a level of at least about 5% within the pH range of from about 4 to about 8. Soluble bismuth-containing pharmaceutical agents include, but are not limited to, bismuth-containing salts, bismuth-containing complexes, and mixtures of bismuth-containing materials with other materials to form a pharmaceutical agent.

Preferred is colloidal bismuth subcitrate. Colloidal bismuth subcitrate ("CBS") is described in *The Merck Index*, 11*th Edition* (1989), item 1296 (incorporated herein by reference in its entirety), to have the approximate molecular formula of $K_3(NH_4)_2[Bi_6O_3(OH)_5(C_6H_5O_7)_4]$. The preparation and use of CBS is described in detail in U.S. Pat. No. 4,801,608, to Bos et al., issued Jan. 31, 1989; and Great Britain patent specification 1,478,742, published Jul. 6, 1977 by Gist-brocades, N.V., the disclosures of both these patents being incorporated herein by reference in their entirety. The CBS mixture used in the compositions of the present invention is preferably in the form of granules, having a preferred particle size of less than about 1.5 mm.

Pharmaceutical compositions of the present invention also preferably comprise as the soluble bismuth-containing agent a pharmaceutically-acceptable salt suitable for oral co-administration of bismuth and an $H_2$ receptor blocking anti-secretory agent. Such pharmaceutically-acceptable salts suitable for oral co-administration of bismuth and an $H_2$ receptor blocking anti-secretory agent comprise bismuth, an organic acid (preferably citrate and tartrate), and an $H_2$ receptor blocking anti-secretory agent (preferably selected from the group consisting of ranitidine or cimetidine).

Preferred pharmaceutically-acceptable salts suitable for oral co-administration of bismuth and an $H_2$ receptor blocking anti-secretory agent are described in European Patent Application Publication No. 282,132, published Sep. 14, 1988 by The Procter & Gamble Company, the disclosures of which are incorporated herein by reference in their entirety. Furthermore, such salts comprising ranitidine are also described in Great Britain Patent Application Publication No. 2,220,937, published Jan. 24, 1990, by Glaxo Group Limited, the disclosures of which are incorporated herein by reference in their entirety.

Preferred pharmaceutically-acceptable salts suitable for oral co-administration of bismuth and an $H_2$ receptor blocking anti-secretory agent are those wherein the organic acid is selected from the group consisting of citrate and tartrate. Thus, preferred salts are those comprising: bismuth, citrate and ranitidine (hereinafter "bismuth-citrate-ranitidine"); bismuth, tartrate and ranitidine (hereinafter "bismuth-tartrate-ranitidine"); bismuth, citrate and cimetidine (hereinafter "bismuth-citrate-cimetidine"); and bismuth, tartrate and cimetidine (hereinafter "bismuth-tartrate-cimetidine").

The soluble bismuth-containing pharmaceutical agent used in the compositions of the present invention (preferably including any optional carrier materials) is preferably in the form of granules or powders, having a preferred particle size of less than about 1.5 mm.

The oral pharmaceutical compositions herein comprise a safe and effective amount of soluble bismuth-containing pharmaceutical agent, typically in the amount of from about 25 mg to about 1000 mg per dosage unit, and preferably from about 25 mg to about 600 mg per dosage unit. As a percentage of the oral pharmaceutical compositions, soluble bismuth-containing pharmaceutical agent typically comprises from about 1% to about 100%, and preferably from about 25% to about 99%, by weight of the composition.

(b) Pharmaceutically-Acceptable Carrier Materials

The oral pharmaceutical compositions herein may also optionally comprise one or more pharmaceutically-acceptable carrier materials. The term "pharmaceutically-acceptable carrier materials," as used herein, means one or more compatible solid or liquid filler diluents or encapsulating substances which are suitable for oral administration to a human or lower animal. The term "compatible," as used herein, means that the components of the oral pharmaceutical composition are capable of being commingled with the soluble bismuth-containing pharmaceutical agent, and with each other, in a manner such that there is no interaction which would substantially reduce the pharmaceutical efficacy of the pharmaceutical composition under ordinary use situations by swallowing the composition. Pharmaceutically-acceptable carrier materials must, of course, be of sufficiently high purity and sufficiently low toxicity to render them suitable for oral administration to the human or lower animal being treated.

To the soluble bismuth-containing pharmaceutical agent may be added any of the pharmaceutically-acceptable carrier materials known in the art, which are compatible with these pharmaceutical agents, such as:

diluents, like lactose, starch, microcrystalline cellulose, sorbitol, mannitol, dibasic calcium phosphate dihydrate, calcium sulfate dihydrate, sucrose-based diluents and mixtures thereof;

binders, like acacia, cellulose derivatives, gelatin, glucose, polyvinylpyrrollidone, starch, sucrose, sorbitol, tragacanth, sodium alginate and mixtures thereof;

disintegrants, like microcrystalline cellulose and cellulose derivatives, starch and its derivatives, alginic acid and its derivatives, ion-exchange resins, cross-linked sodium carboxymethyl cellulose, sodium starch glycolate, cross-linked polyvinylpyrrollidone and formaldehyde-caseine;

lubricants, antiadherents and glidants, like magnesium-, calcium- and sodium stearates, stearic acid, hydrogenated castor oil, talc, water, polyethylene glycol, sodium laryl sulfate, magnesium laryl sulfate and silica.

Furthermore, the pharmaceutically-acceptable carrier materials may also comprise one or more auxiliary medicaments, preferably those which are intended to act in combination with it, such as non-steroidal anti-inflammatory compounds, H$_2$-antagonists, cytoprotectants (e.g., sucralfate), and synthetic prostaglandins. In particular the dosage units may contain antimicrobially effective medicaments such as antibiotics and chemotherapeutic compounds, more in particular medicaments effective against *Campylobacter pylori* (recently renamed *Helicobacter pylori*), such as the antimicrobially effective imidazoles, in particular metronidazole and tinidazole, penicillins, cephalosporins, tetracyclines, chinolones and macrolides. The dosage of the optionally present auxiliary medicaments will depend on the effectivity of the particular medicament used. Optional auxiliary medicaments useful herein are described in detail in: European Patent Application Publication No. 206,625, published Dec. 30, 1986, by Marshall; and International Publication No. WO 86/05981, published Oct. 23, 1986, by Borody; and European Patent Application Publication No. 282,131, published Sep. 14, 1988, by The Procter & Gamble Company; the disclosures of all these publications being incorporated herein by reference in their entirety.

The most preferred oral dosage units according to the invention are capsules, although tablets having a low density as defined above are also possible. The material of swallowable capsules according to the invention may be any of those known in the art, such as gelatine, modified starches, such as hydroxyalkyl starch, and cellulose derivatives, such as cellulose ethers, e.g. methyl cellulose. Preferably, the capsule material and size of the capsule are chosen such that the capsule unit dosage form filled with the drug mixture has a density of less than about 1 g/ml. Gelatine capsules can be soft and hard. The dosage units according to the invention may be further coated in order to provide for controlled release.

As a percentage of the oral pharmaceutical compositions, pharmaceutically-acceptable carrier materials comprise from about 0% to about 99%, and preferably from about 1% to about 75%, by weight of the composition.

The method of manufacturing unit dosage forms suitable for swallowing comprising a soluble bismuth-containing pharmaceutical agent, according to the present invention, preferably comprises the step of forming a unit dosage of a dry composition comprising a soluble bismuth-containing pharmaceutical agent having a packing density of less than about 1 g/ml. Preferred is the method wherein a dry particulate composition (e.g., granulate; powder) comprising a soluble bismuth-containing pharmaceutical agent is filled into a capsule to a packing density of less than about 1 g/ml.

(2) Methods for Treating or Preventing Gastrointestinal Disorders

Another aspect of the present invention is methods for treating or preventing gastrointestinal disorders in humans or lower animals. Such methods comprise orally administering by swallowing, to a human or lower animal in need of such treatment or prevention, a safe and effective amount of an oral pharmaceutical composition according to the present invention.

The term "gastrointestinal disorder," as used herein, encompasses any disease or other disorder of the gastrointestinal tract, preferably the upper gastrointestinal tract, of a human or lower animal treatable or preventable by the bismuth-containing agents useful herein.

The term "upper gastrointestinal tract," as used herein, is defined to include the esophagus, the stomach, the duodenum, and the jejunum. Such upper gastrointestinal tract disorders include, for example: disorders not manifested by presence of ulcerations in the gastric mucosa (herein "non-ulcerative gastrointestinal disorders"), including chronic or atrophic gastritis, non-ulcer dyspepsia, esophageal reflux disease and gastric motility disorders; and "peptic ulcer disease," i.e., gastric, duodenal and jejunal ulcers. Included herein are diseases or disorders caused or mediated by *Helicobacter pylori*.

The phrase "safe and effective amount," as used herein, means an amount of the soluble bismuth-containing pharmaceutical agent high enough to significantly positively modify the condition to be treated but low enough to avoid serious side effects (at a reasonable benefit/risk ratio), within the scope of sound medical judgement. The safe and effective amount of the oral pharmaceutical composition of the present invention will vary with the particular condition being treated, the age and physical condition of the patient being treated, the severity of the condition, the duration of treatment, the nature of concurrent therapy, the particular pharmaceutically-acceptable carrier materials utilized, and like factors within the knowledge and expertise of the attending physician. The methods of the present invention typically involve administering from about 50 mg to about 5000 mg of the pharmaceutically-acceptable salt per day, and preferably from about 100 mg to about 1500 mg per day.

The following examples further described and demonstrate the present invention. The examples are given solely for the purpose of illustration, and are not to be construed as limitations of the present invention since many variations thereof are possible without departing from its spirit and scope.

EXAMPLE 1

A bismuth-citrate-ranitidine salt as described in European Patent Application Publication No. 282,132 and Great Britain Patent Application Publication No. 2,220,937 is used to prepare capsules as follows.

217 kg of bismuth-citrate-ranitidine is granulated with 23.8 kg of corn starch using 5.85 kg of povidone K30 dissolved in 51.0 kg of ethanol. The granulate, having a particle size of less than 1.5 mm, is blended with 7.8 kg of polacrilin potassium, 1.98 kg of polyethylene glycol 6000 and 0.66 kg of magnesium stearate. This granulate (420 mg) is filled into hard gelatin capsules No. 0, using a rotary capsule filling machine. The packing density of the capsule content is adjusted to about 0.6 g of bismuth-citrate-ranitidine composition/ml by settings of the piston within the dosator.

Administration of 2 of these capsules (710 mg bismuth-citrate-ranitidine; approximately 30% bismuth), by swallowing, to humans gives lower systemic bismuth absorption than do unit dosage forms having packing density above about 1 g/ml.

What is claimed is:

1. An oral pharmaceutical composition in unit dosage form suitable for swallowing comprising a safe and effective amount of a soluble bismuth-containing pharmaceutical agent, and optionally pharmaceutically-acceptable carrier materials, wherein the packing density of the pharmaceutical composition is less than about 1 g/ml.

2. The oral pharmaceutical composition according to claim 1 wherein the soluble bismuth-containing pharmaceutical agent is selected from pharmaceutically-acceptable salts suitable for oral co-administration of bismuth and an $H_2$ receptor blocking anti-secretory agent, wherein said salts comprise bismuth, an organic acid and an $H_2$ receptor blocking anti-secretory agent selected from the group consisting of ranitidine and cimetidine.

3. The oral pharmaceutical composition according to claim 2 wherein the packing density is within the range of from about 0.05 g/ml to less than about 1 g/ml.

4. The oral pharmaceutical composition according to claim 3 wherein the organic acid of the pharmaceutically-acceptable salt is selected from the group consisting of citrate, tartrate, and mixtures thereof.

5. The oral pharmaceutical composition according to claim 2 further comprising at least one auxiliary medicament.

6. The oral pharmaceutical composition according to claim 5 further comprising at least one antimicrobial medicament safe and effective against *Helicobacter pylori*.

7. An oral pharmaceutical composition in unit dosage form suitable for swallowing comprising:
   (a) from about 1% to about 100%, by weight of the composition, of a pharmaceutically-acceptable salt suitable for oral co-administration of bismuth and an $H_2$-receptor blocking anti-secretory agent, wherein said salt comprises bismuth, an organic acid and an $H_2$-receptor blocking anti-secretory agent selected from the group consisting of ranitidine and cimetidine; and
   (b) from about 0% to about 99%, by weight of the composition, pharmaceutically-acceptable carrier materials;
and wherein the packing density of the pharmaceutical composition is less than about 1 g/ml.

8. The oral pharmaceutical composition in unit dosage form according to claim 7 comprising a pharmaceutically-acceptable salt selected from the group consisting of bismuth-citrate-ranitidine, bismuth-citrate-cimetidine, bismuth-tartrate-ranitidine, bismuth-tartrate-cimetidine, and mixtures thereof.

9. The oral pharmaceutical composition in unit dosage form according to claim 8 comprising:
   (a) from about 25% to about 99%, by weight of the composition, of the pharmaceutically-acceptable salt; and
   (b) from about 1% to about 75%, by weight of the composition, pharmaceutically-acceptable carrier materials;
and wherein the packing density of the pharmaceutical composition is within the range of from about 0.05 g/ml to less than about 1 g/ml.

10. The oral pharmaceutical composition according to claim 9 in unit dosage form of a capsule.

11. The oral pharmaceutical composition according to claim 7 comprising at least one antimicrobial medicament safe and effective against *Helicobacter pylori*.

12. The oral pharmaceutical composition according to claim 11 further comprising at least one antimicrobial medicament effective against *Helicobacter pylori* selected from the group consisting of metronidazole, tinidazole, penicillin, cephalosporin, tetracycline, chinolones, macrolides, or mixture thereof.

13. An oral pharmaceutical composition in unit dosage form of a capsule suitable for swallowing comprising:
   (a) from about 25% to about 99%, by weight of the composition, of a pharmaceutically-acceptable salt comprising bismuth, citrate and ranitidine; and
   (b) from about 1% to about 75%, by weight of the composition, pharmaceutically-acceptable carrier materials;
and wherein the pharmaceutical composition is filled into a capsule to a packing density within the range of from about 0.5 g/ml to about 0.75 g/ml.

14. The oral pharmaceutical composition according to claim 13 wherein the dosage units are capsules selected from the group consisting of gelatin, modified starch and cellulose derivative, and wherein further the capsule dosage unit has a packing density of less than about 1 g/ml.

15. The oral pharmaceutical composition according to claim 13 further comprising at least one antimicrobial medicament effective against *Helicobacter pylori* selected from the group consisting of metronidazole, tinidazole, penicillin, cephalosporin, tetracycline, chinolones, macrolides, or mixture thereof.

16. A method for treating or preventing gastrointestinal disorders in humans or lower animals, said method comprising orally administering by swallowing to a human or lower animal in need of such treatment or prevention a safe and effective amount of an oral pharmaceutical composition according to claim 1.

17. A method for treating or preventing gastrointestinal disorders in humans or lower animals, said method comprising orally administering by swallowing to a human or lower animal in need of such treatment or prevention a safe and effective amount of an oral pharmaceutical composition according to claim 2.

18. A method for treating or preventing gastrointestinal disorders in humans or lower animals, said method comprising orally administering by swallowing to a human or lower animal in need of such treatment or prevention a safe and effective amount of an oral pharmaceutical composition according to claim 4.

19. A method for treating or preventing gastrointestinal disorders in humans or lower animals, said method comprising orally administering by swallowing to a human or lower animal in need of such treatment or prevention a safe and effective amount of an oral pharmaceutical composition according to claim 6.

20. A method for treating or preventing gastrointestinal disorders in humans or lower animals, said method comprising orally administering by swallowing to a human or lower animal in need of such treatment or prevention a safe and effective amount of an oral pharmaceutical composition according to claim 8.

21. A method for treating or preventing gastrointestinal disorders in humans or lower animals, said method comprising orally administering by swallowing to a human or lower animal in need of such treatment or prevention a safe and effective amount of an oral pharmaceutical composition according to claim 11.

22. A method for treating or preventing gastrointestinal disorders in humans or lower animals, said method comprising orally administering by swallowing to a human or lower animal in need of such treatment or prevention a safe and effective amount of an oral pharmaceutical composition according to claim 13.

23. A method for treating or preventing gastrointestinal disorders in humans or lower animals, said method comprising orally administering by swallowing to a human or lower animal in need of such treatment or prevention a safe and effective amount of an oral pharmaceutical composition according to claim 15.

24. A method for manufacturing unit dosage forms suitable for swallowing, said method comprising the step of forming a unit dosage of a dry composition comprising a soluble bismuth-containing pharmaceutical agent having a packing density of less than about 1 g/ml.

25. The method according to claim 24 wherein a dry particulate composition comprising a soluble bismuth-containing pharmaceutical agent is filled into a capsule to a packing density of less than about 1 g/ml.

26. The method according to claim 25 wherein the soluble bismuth-containing pharmaceutical agent is selected from pharmaceutically-acceptable salts suitable for oral co-administration of bismuth and an $H_2$ receptor blocking anti-secretory agent, wherein said salts comprise bismuth, an organic acid and an $H_2$ receptor blocking anti-secretory agent selected from the group consisting of ranitidine and cimetidine.

27. The method according to claim 26 wherein the soluble bismuth-containing pharmaceutical agent is bismuth-citrate-ranitidine.

* * * * *